United States Patent [19]

Friedheim

[11] 4,151,188
[45] Apr. 24, 1979

[54] ARSENAMIDE COMPOUND

[76] Inventor: Ernst A. H. Friedheim, 5, Ave. Marc Monnier, Geneva, Switzerland

[21] Appl. No.: 488,067

[22] Filed: Jul. 12, 1974

Related U.S. Application Data

[60] Division of Ser. No. 380,364, Jul. 18, 1973, Pat. No. 3,856,971, which is a continuation-in-part of Ser. No. 339,843, Mar. 9, 1973, Pat. No. 3,842,171.

[51] Int. Cl.² .................... C07F 9/78; A61K 31/285
[52] U.S. Cl. ................................... 260/440; 424/297
[58] Field of Search .................... 424/297; 260/440

[56] References Cited
U.S. PATENT DOCUMENTS 3,247,056  4/1966  Epstein ............................ 424/297
3,485,860  12/1969  Klingsberg ...................... 424/297

*Primary Examiner*—Sam Rosen
*Attorney, Agent, or Firm*—Stevens, Davis, Miller & Mosher

[57] ABSTRACT

There is disclosed an arsenamide compound of the formula

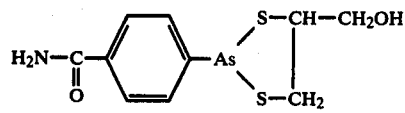

The compound is useful in combatting filariasis due to *D. immitis* in dogs.

1 Claim, No Drawings

ARSENAMIDE COMPOUND

This application is a division of Ser. No. 380,364 filed July 18, 1973, now U.S. Pat. No. 3,856,971, which is a continuation-in-part of application Ser. No. 339,843 filed Mar. 9, 1973, now U.S. Pat. No. 3,842,171.

The present invention is concerned with a method of combating filariasis due to D. immitis in dogs by administrating to a dog certain arsenic compounds as defined hereafter.

The causal treatment of diseases caused by filaria requires according to the present state of science, two drugs, one of which acts upon the adult worms (macrofilaria) and the other on the embryonic forms (microfilaria). For the destruction of the adult worms preparations containing arsenic are available, but they are limited in their use in as far as they have to be applied via the parenteral route. Two currently used compounds, thioacetarsamide and oxychlorophenarsin (Mapharsen) have to be applied strictly intravenously, because they produce inflammatory reactions and necrosis when applied by subcutanous and intramuscular fashion.

It is an object of this invention to provide an effective drug against filariasis in the dog, which drug can be given orally.

It has now been found that certain phenylarsenoxides and their mercaptides, when given orally, are well tolerated in therapeutic doses by dogs and kill the adult worms of Dirafilaria immitis in the blood of infected dogs.

According to the present invention, the method of combating filariasis due to D. immitis in dogs comprises administering to a dog a pharmaceutically effective amount of a compound of the formula I

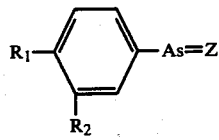

I wherein Z is oxygen or a group of the formula $$-S-CH-CH_2OH$$
$$\,|$$
$$-S-CH_2$$

or Z represents two groups of the formula

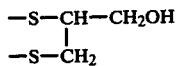

$R_1$ is —OH, —NH.CO.NH$_2$, —CO.NH$_2$, —CH$_2$—CO.NH$_2$ and $R_2$ is hydrogen, —NH$_2$ or —NH.CO.CH$_3$ The new technical effect achieved by oralmacrofilaricidal therapy consists of the practical advantages of a therapy obviating the use of syringes and injections under aseptic conditions requiring trained personnel.

A further advantage of the present invention is presented by particular galenic forms allowing orally active macrofilaricidal agents to be applied together with orally active microfilaricidal agents such as the compounds known under the names of Diethylcarbamazine (Hetrazan) and Dithazanine Iodide, as well as the optical isomers of Tetramisole (Merck Index 1968, 1029)

The compounds according to formula I can be applied, as dry powder in bulk, or contained in capsules, tablets, dragees, or dissolved or suspended or emulgated in a pharmaceutically acceptable liquid non-aqueous medium, e.g. propyleneglycol, ethyl-oleate, benzyl alcohol, salicylic alcohol (Saligenine) oils including olive-, sesame, cottonseed-, peanut oil, and mixtures thereof, if desired with additives affecting advantageously dispersion, emulsion, stability, taste.

For oral application the compounds according to formula I may be mixed in to the food of the animals to be treated, in form of dry powder, or in solution, suspension, emulsion as stated in the foregoing paragraph, if desired with a taste improving additive.

Solutions in propyleneglycol are added to the food preferably after dilution with 1–10 volumes of water.

In a preferred form of the present invention the macrofilaricidal compounds according to formula I may be mixed with microfilaricidal agents, e.g. Diethylcarbamazine or Dithazanine for simultaneous oral application, in dry state or in solution, suspension, emulsion in organic liquids as stated above.

It is understood that the quantities and concentrations of compounds according to formula I when applied as such may vary in wide limits, e.g. between 0.05 and 0.60 g per unit of dry powder in capsules, tablets, dragees, and the concentrations in solutions and suspensions etc. e.g. between 0.1 and 6.0%.

The proportion of compounds according to formula I and microfilaricidal compounds, e.g. Diethylcarbamazine and Dithazanine iodide, in mixtures, may range from 1:1 to 1:10 or 1:1 to 10:1.

The dosage for the oral treatment of canine filariasis with compounds of formula I ranges from 2–50 mg/kg for the single dose. The dosage of Diethylcarbamazine is known to range from 50–100 mg/kg, and the dosage of Dithazanine 5–10 mg/kg for the single dose in canine filariasis. Tetramisole dosage 2–10 mg/kg Examples for oral macrofilaricidal activity of compounds according to formula I are recorded in table I. It appears that these compounds reduce the number of living adult worms significantly, in certain cases to zero.

These compounds have little direct effect on microfilaria.

The microfilaricidal effect of Diethylcarbamazine and Dithazanine iodide are known.

The macrofilaricidal oral application of compounds according to formula I, can be associated with parenteral applications of microfilaricidal agents such as Hoe 33 258 and fention (Bayer 29 493, Baytex etc).

TABLE

Number of living specimens of Dirafilaria immitis found at autopsy of naturally infected dogs, 35 days after oral treatment with a substituted phenylarsenoxide or mercaptides thereof with one dose a day for 5 consecutive days. Dogs were killed at the end of the observation period with intravenous phenobarbital.

| dog | | | single dose | living filaria p.m. | | |
| No | kg | substance | mg/kg | m | f | total |
| 7 | 19.1 | Arsenamid B | 5 | 21 | 17 | 33 |
| 8 | 9.5 | " | 10 | 18 | 2 | 20 |
| 9 | 21.1 | Carbason B | 10 | 14 | 5 | 19 |
| 10 | 23 | " | 20 | 9 | 2 | 11 |
| 11 | 17 | Mapharsen | 2 | 23 | 16 | 39 |

-continued

| dog | | single dose | living filaria p.m. | | |
|---|---|---|---|---|---|
| No | kg | substance | mg/kg | m | f | total |
| 12 | 15 | " | 4 | 16 | 5 | 21 |
| 13 | 18 | Mapharsen B | 3 | 33 | 16 | 49 |
| 14 | 19.5 | " | 6 | 4 | 0 | 4 |
| 15 | 20.7 | — | — | 18 | 13 | 31 |
| 16 | 21.4 | — | — | 22 | 28 | 40 |
| 17 | 18.9 | — | — | 10 | 10 | 20 |
| 18 | 22.3 | — | — | 6 | 7 | 13 |

The various compounds mentioned above have the following formulas:

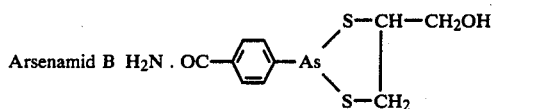

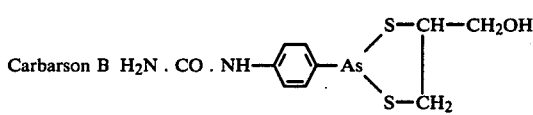

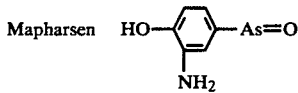

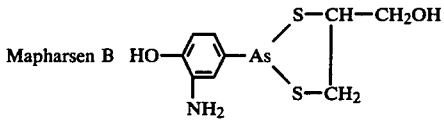

Diethylcarbamazine = 1-diethylcarbamoyl-4-methyl-piperazine

Dithazanine = 3,3'-diethyl-thiadicarboxycyanine (iodide).

The abovementioned Arsenamid B is a novel compound. It can be prepared by reacting p-carboxamidophenyl arsenoxide with 2,3-dimercapto-propanol-1. A more suitable manner for preparing Arsenamid B consists in reacting a dithioglycolate of p-carboxamidophenyl arsenoxide with 2,3-dimercapto-propanol-1. The reaction scheme is as follows:

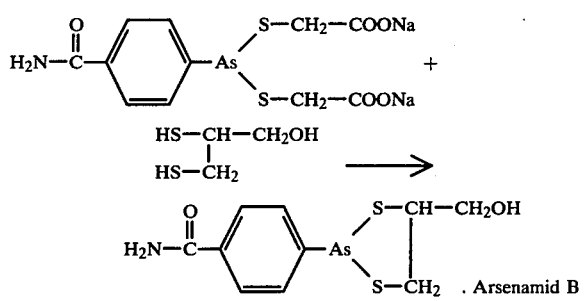

EXAMPLE 50 g (0.13 mol) of bis(carboxymethylmercapto) (p-carbamoylphenyl)arsine (known as "Caparsolate") and dissolved in 800 ml MeOH and 37 ml concentrated aqueous ammonia, to give a solution of pH 8–9. 16.5 g 2,3-dimercaptopropanol (0.13 mol) dissolved in 40 mol MeOH are added. The filtered solution is run with stirring into 3000 ml of icewater. The white precipitate formed is filtered off, washed with 25% aqueous MeOH and dried in vacuum. Yield: 30 g. The product is Arsenamide B of the formula indicated above. It is a white crystaline powder, insoluble in water, cold MeOH, EtOH, acetone, ether, chloroform, sparingly soluble in hot MeOH, EtOH, soluble in dimethylformamide, dimethylsulfoxide, glacial acetic acid.

Tablets (a) 1 Part by weight of Arsenamide B and 5 parts by weight of a pharmaceutical acceptable filler (excipient), preferably starch, are mechanically blended and worked with water into a paste. In a conventional procedure the paste is granulated by passing through a mesh and the dried granules are fed into a tableting machine set to produce tablets containing 50, 100 and 200 mg of Arsenamide B.

The proportion of active ingredient to filler may be varied from 1:1 to 1:30. Other fillers may be used including lactose, talc, caseine. Other liquids than water may be used for granulating including alcohol and acetone, and mixtures of alcohol and acetone with water. Under appropriate mecanical conditions the step of granulating may be omitted and the mixture of active ingredient and filler compressed directly, with or without addition of a binder such as gum arabic, to tablets. The weight of active ingredient per tablet may range from 50–500 mg. The tablets may be coated by conventional procedures, including coatings preventing the disintegration of the tablets in the stomach.

The tablets may be made to contain in addition to compounds according to formula I, other filaricidal agents including Hetrazan, Dithiazanine Iodide and Levamisole.

(b) 1 Part by weight of Arsenamide and 1 part by weight of Levamisole are blended with 10 parts by weight of lactose, worked to a paste with 50% alcohol, granulated and tableted as in the preceding example (a), to tablets containing 50, 100 or 200 mg of each of the two active ingredients.

In the foregoing examples (a) and (b) Arsenamide B may be replaced by other compounds according to formula I, including Carbasone B, and levamisole may be replaced by Hetrazan and Dithiazanine Iodide.

I claim:

1. The compound of the formula

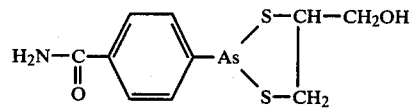

* * * * *